US010398554B2

(12) United States Patent
Ladjali (10) Patent No.: US 10,398,554 B2
(45) Date of Patent: Sep. 3, 2019

(54) DEVICE FOR TREATMENT OF BODY TISSUE, AND ASSOCIATED TREATMENT KIT

(71) Applicant: Mustapha Ladjali, Rueil Malmaison (FR)

(72) Inventor: Mustapha Ladjali, Rueil Malmaison (FR)

(73) Assignee: Mustapha Ladjali, Rueil Malmaison (FR)

(*) Notice: Subject to any disclaimer, the term of this patent is extended or adjusted under 35 U.S.C. 154(b) by 0 days.

(21) Appl. No.: 14/895,578

(22) PCT Filed: Jun. 5, 2014

(86) PCT No.: PCT/EP2014/061742
§ 371 (c)(1),
(2) Date: Dec. 3, 2015

(87) PCT Pub. No.: WO2014/195422
PCT Pub. Date: Dec. 11, 2014

(65) Prior Publication Data
US 2016/0128832 A1    May 12, 2016

(30) Foreign Application Priority Data

Jun. 5, 2013  (FR) .................................. 13 55180

(51) Int. Cl.
*A61B 17/122*    (2006.01)
*A61F 2/24*       (2006.01)
*A61B 17/128*    (2006.01)

(52) U.S. Cl.
CPC ........ *A61F 2/2454* (2013.01); *A61B 17/1227* (2013.01); *A61B 17/1285* (2013.01); *A61F 2/2463* (2013.01); *A61F 2/2466* (2013.01)

(58) Field of Classification Search
CPC ...... A61F 2/246; A61F 2/2463; A61F 2/2454; A61B 17/08; A61B 17/083; A61B 17/122; A61B 17/1227
USPC .................................. 606/151; 623/2.1–2.42
See application file for complete search history.

(56) References Cited

U.S. PATENT DOCUMENTS

| | | | | |
|---|---|---|---|---|
| 5,242,456 A | * | 9/1993 | Nash | A61B 17/0218 606/139 |
| 5,507,811 A | * | 4/1996 | Koike | A61B 17/0057 606/151 |
| 5,972,022 A | * | 10/1999 | Huxel | A61B 17/0401 606/215 |

(Continued)

FOREIGN PATENT DOCUMENTS

EP    2123227 A1    11/2009
EP    2591754 A1     5/2013

OTHER PUBLICATIONS

International Search Report dated Jul. 7, 2014 issued in corresponding PCT Application No. PCT/EP2014/061742.

*Primary Examiner* — Kathleen S Holwerda
(74) *Attorney, Agent, or Firm* — Troutman Sanders LLP (57) ABSTRACT

A device for treating a body tissue having a prolapse comprising two clamping assemblies, each clamping assembly being able to clamp a free edge of the body tissue on either side of the prolapse, and a membrane connecting both clamping assemblies to each other, the membrane being able to be held taut facing the prolapse by both clamping assemblies, is provided herein.

8 Claims, 8 Drawing Sheets

(56) References Cited

U.S. PATENT DOCUMENTS

| | | | |
|---|---|---|---|
| 6,702,826 B2 * | 3/2004 | Liddicoat | A61B 17/00234 606/151 |
| 7,635,329 B2 * | 12/2009 | Goldfarb | A61B 17/0401 600/37 |
| 2003/0120340 A1 * | 6/2003 | Liska | A61F 2/2454 623/2.1 |
| 2005/0038509 A1 | 2/2005 | Ashe | |
| 2005/0159810 A1 * | 7/2005 | Filsoufi | A61F 2/2463 623/2.1 |
| 2009/0254103 A1 * | 10/2009 | Deutsch | A61F 2/2481 606/151 |
| 2011/0060407 A1 | 3/2011 | Ketai et al. | |
| 2012/0197388 A1 | 8/2012 | Khairkhahan et al. | |
| 2013/0023985 A1 | 1/2013 | Khairkhahan et al. | |

\* cited by examiner

DEVICE FOR TREATMENT OF BODY TISSUE, AND ASSOCIATED TREATMENT KIT

CROSS-REFERENCE TO RELATED APPLICATIONS

This application is the U.S. National Phase of International Patent Application Serial No. PCT/EP2014/061742, filed Jun. 5, 2014, which claims priority to French Patent Application No. 13 55180, filed Jun. 5, 2013, the contents of each of which are incorporated herein by reference in their entirety.

FIELD OF THE INVENTION

The present invention relates to a treatment device a body tissue having a prolapse.

BACKGROUND OF THE INVENTION

This device is notably applied to the treatment of cardiac valves, and in particular to the treatment of mitral valves.

A mitral valve typically consists of two leaflets, anterior and posterior leaflets, and controls the blood flow which flows from the left auricle to the left ventricle of the heart. The mitral valve ensures one-way circulation of the blood flow, avoiding blood backflow at the end of the ventricular contraction.

In order to avoid blood backflow, the leaflets of the valve should ensure coaptation with their free edges.

In the case of a prolapse, i.e. of relaxation of the wall of the leaflet, one of the leaflets has a bulge which defines a thickened and surface-increased protruding area. The prolapse may then prevent the valve from closing sealably. The result of this is mitral insufficiency, i.e. a backflow of blood into the left auricle when the ventricle contracts.

A possible treatment of this disease consists in surgical ablation of the prolapse. However, such an invasive operation is tedious and has non-negligible risks for the patient, notably when the patient is elderly and/or with a bad health.

In order to overcome this problem, another known means for treating this disease endovascularly consists of placing a clip intended to form a connecting point between the anterior leaflet and the posterior leaflet, at the prolapse. This gives the possibility of re-establishing coaptation between the leaflets of the valve at the prolapse.

However, the clip forms a permanent connecting point between the leaflets of the valve. Thus, when the valve opens, the leaflets only open on either side of the connecting point generating two apertures with distinct passages. The blood then flows through two routes separated from each other by the connecting point.

This type of treatment suppresses the problem at the prolapse. However, it does not give entire satisfaction, since it perturbs the coaptation of the leaflets away from the prolapse, and since it perturbs the passing of the blood at the valve.

SUMMARY OF THE INVENTION

An object of the invention is therefore to obtain a device for treating a body tissue having a prolapse giving the possibility of treating the prolapse in a not very invasive way, by perturbing as less as possible the tissue once the clamp has been placed.

In particular, when the tissue is a cardiac valve leaflet, an object of the invention is to treat the prolapse by allowing the valve to close sealably when the ventricle contracts, and by ensuring satisfactory coaptation of the leaflets.

For this purpose, the subject-matter of the invention is a device for treatment of a body tissue having a prolapse, characterized in that it includes two clamping assemblies, each clamping assembly being able to clamp a free edge of the body tissue on either side of the prolapse, the device comprising a membrane connecting both clamping assemblies to each other, the membrane being able to be maintained in tension facing the prolapse by both clamping assemblies.

The treatment device according to the invention may comprise one or several of the following features, taken individually or according to any technically possible combination:

- each clamping assembly comprises an arm for clamping the free edge of the body tissue, the clamping arm comprising a first flexible distal end with the shape of a hook;
- each clamping assembly comprises a member for locking the first distal end around the free edge of the body tissue, the locking member having a second distal end with the shape of a hook, the locking member being movable relatively to the clamping arm between a rest position in which the second distal end is at a distance from the first distal end, and a locking position in which the second distal end exerts a force on the hook of the first distal end so as to lock the hook of the first distal end around the free edge of the body tissue;
- each clamping assembly comprises an assembling element capable of maintaining assembled the locking member and the clamping arm;
- each assembling element is formed by a gutter, the gutter being connected to the clamping arm, the locking member extending inside the gutter parallel to the clamping arm; and
- each assembling element is formed with at least one hoop attached on the clamping arm, the locking member extending parallel to the clamping arm between the clamping arm and said or each hoop.

The object of the invention is also a kit for treating a body tissue having a prolapse, comprising:

- a treatment device as described above;
- a supporting member capable of retaining the treatment device; and
- a supporting rod extending along a longitudinal axis and defining at least one aperture for retaining the supporting member.

The treatment kit according to the invention may comprise one or several of the following features, taken individually or according to any technically possible combination:

- the kit comprises maneuvering member a movable relatively to the supporting rod for maneuvering the prolapse from a position close to the membrane to a position away from the membrane;
- the supporting member comprises two fingers each defining a housing capable of receiving a clamping assembly, each finger comprising a slot intended to be crossed by the membrane; and
- the supporting rod comprises a first compartment and a second compartment, the first and second compartments extending along the longitudinal axis, the first compartment retaining the supporting member, the second compartment retaining the maneuvering member.

The invention further relates to a method for treating a body tissue having a prolapse, comprising the steps:

providing a treatment kit as defined earlier;

displacing the supporting member along the longitudinal axis towards the outside of the supporting rod;

positioning the first distal ends of the clamping arms each around the free edge of the body tissue on either side of the prolapse, the locking members being in the rest position;

displacing the prolapse away from the membrane via the maneuvering member;

displacing the locking members towards the locking position so as to lock the hooks of the first distal ends around the free edge of the body tissue.

The treatment method according to the invention may further comprise the feature according to which the body tissue is a valve leaflet, advantageously a mitral valve leaflet.

BRIEF DESCRIPTION OF THE DRAWINGS

The invention will be better understood upon reading the description which follows, only given as an example and made with reference to the appended drawings wherein.

DETAILED DESCRIPTION OF THE INVENTION

In all the following, the terms of "proximal" and "distal" are respectively understood as relatively close to the operator, and as relatively closer away from the operator. The terms "upper" and "lower" are meant relatively to the orientations illustrated in the figures.

Figures 1, 2:
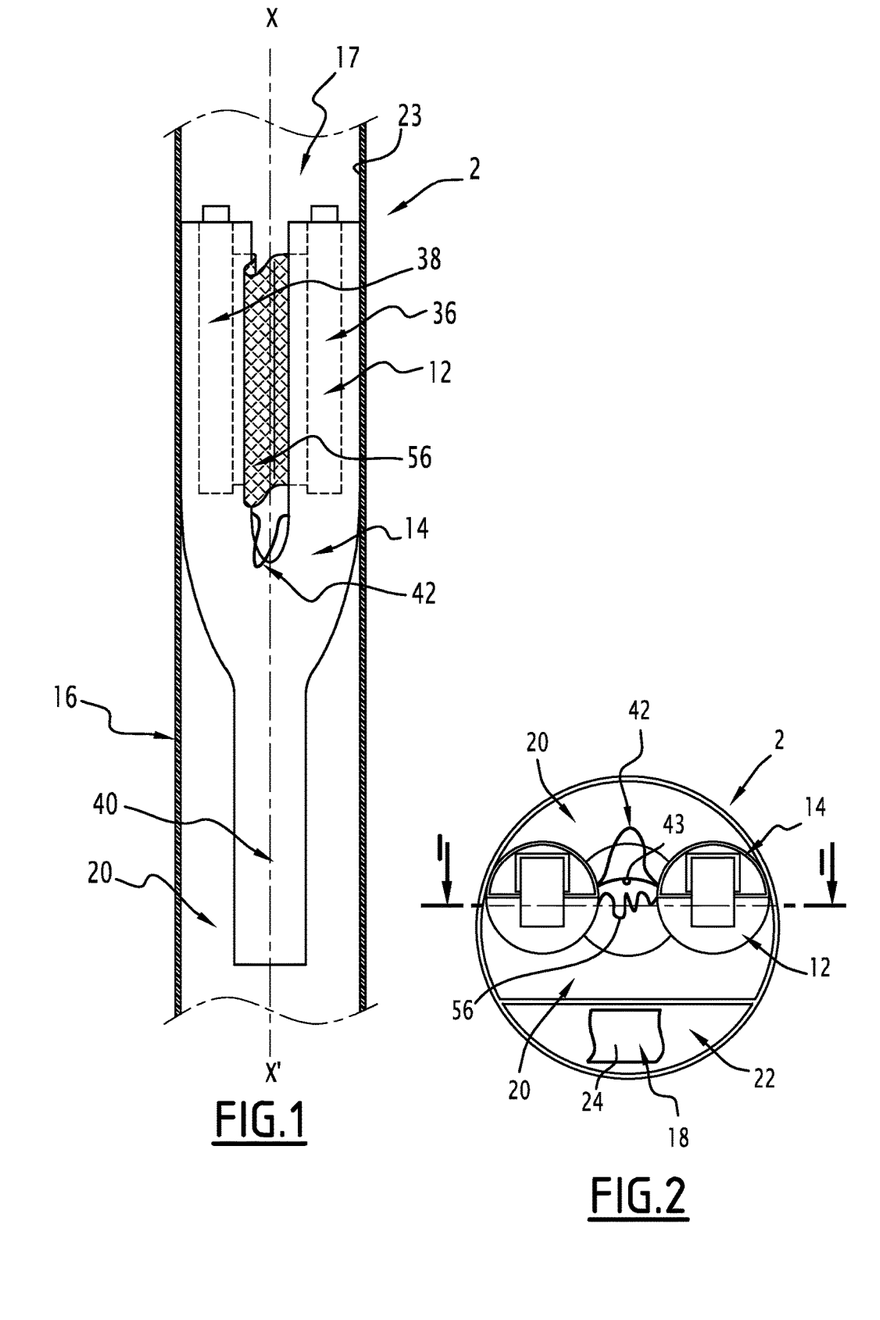
FIG. 1 is a partial sectional view of a treatment kit according to the invention.
FIG. 2 is a top view of a treatment kit according to the invention.

A treatment kit 2 according to the invention is illustrated in FIGS. 1 and 2.

This treatment kit 2 is intended for treating a body tissue having a prolapse, notably for treating a cardiac valve such as a mitral valve.

Figures 3, 4, 5:
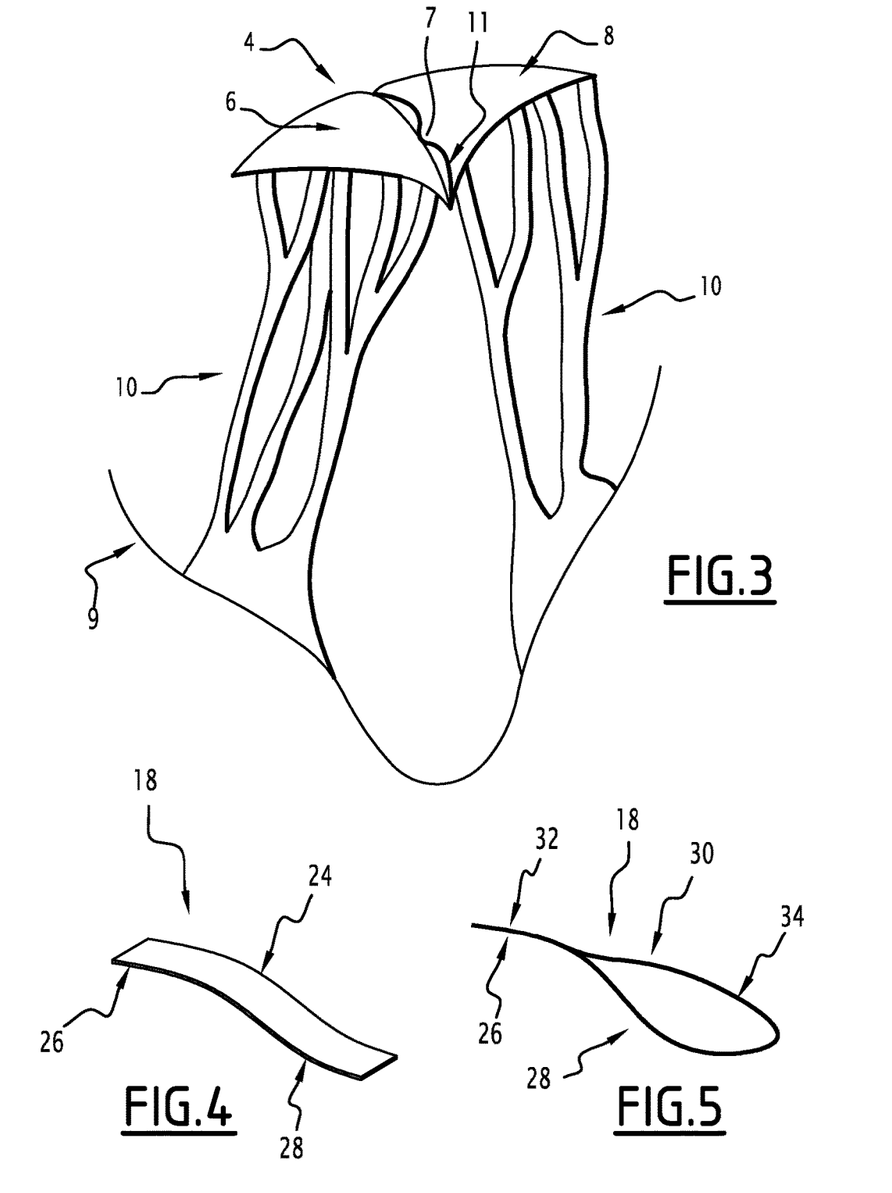
FIG. 3 is a schematic illustration of a cardiac valve having a prolapse.
FIG. 4 is a schematic illustration of a maneuvering member according to a first embodiment of the invention.
FIG. 5 is a member for maneuvering the prolapse according to an alternative embodiment of the invention.

Such a valve 4 is illustrated in FIG. 3. It is typically formed with an anterior leaflet 6 and a posterior leaflet 8. In this example, the prolapse 7 is located on the posterior leaflet 8. The leaflets 6, 8 of the valve 4 are connected to the wall 9 of the left ventricle via cords 10.

The prolapse 7 forms a bulge which protrudes at the free edge 11 of the posterior leaflet 8 preventing coaptation between the free edges of the leaflets 6, 8 of the valve 4.

As illustrated by FIGS. 1 and 2, the treatment kit 2 according to the invention comprises a treatment device 12, a supporting member 14 and a supporting rod 16. The supporting member 14 is able to retain the treatment device 12. The supporting rod 16 extends along a longitudinal axis XX' and defines a distal aperture 17 for retaining the supporting member 14.

The treatment kit 2 further comprises a member 18 for maneuvering the prolapse 7.

As illustrated by FIG. 2, the supporting rod 16 includes a first side compartment 20 and a second side compartment 22.

The first compartment 20 is intended to house the supporting member 14. It comprises a maintaining internal surface 23 able to maintain the supporting member 14 fixed in rotation relatively to the longitudinal axis XX' of the supporting rod 16.

The second compartment 22 is intended to house the member 18 for maneuvering the prolapse 7. The maneuvering member 18 is freely slidably mounted inside the second compartment 22 of the supporting rod 16.

In the example illustrated in FIG. 4, the maneuvering member 18 is a tab 24 having an elongated shape with the shape of the back of a spoon, and defining a grasping area 26 and an area 28 for maneuvering the prolapse 7 opposite to the grasping area 26.

Alternatively and as illustrated by FIG. 5, the maneuvering member 18 is a rigid wire 30 comprising an elongated portion 32 defining the grasping area 26. The maneuvering area 28 is defined by a loop 34 formed by the wire 30 curved on itself.

Figure 6:
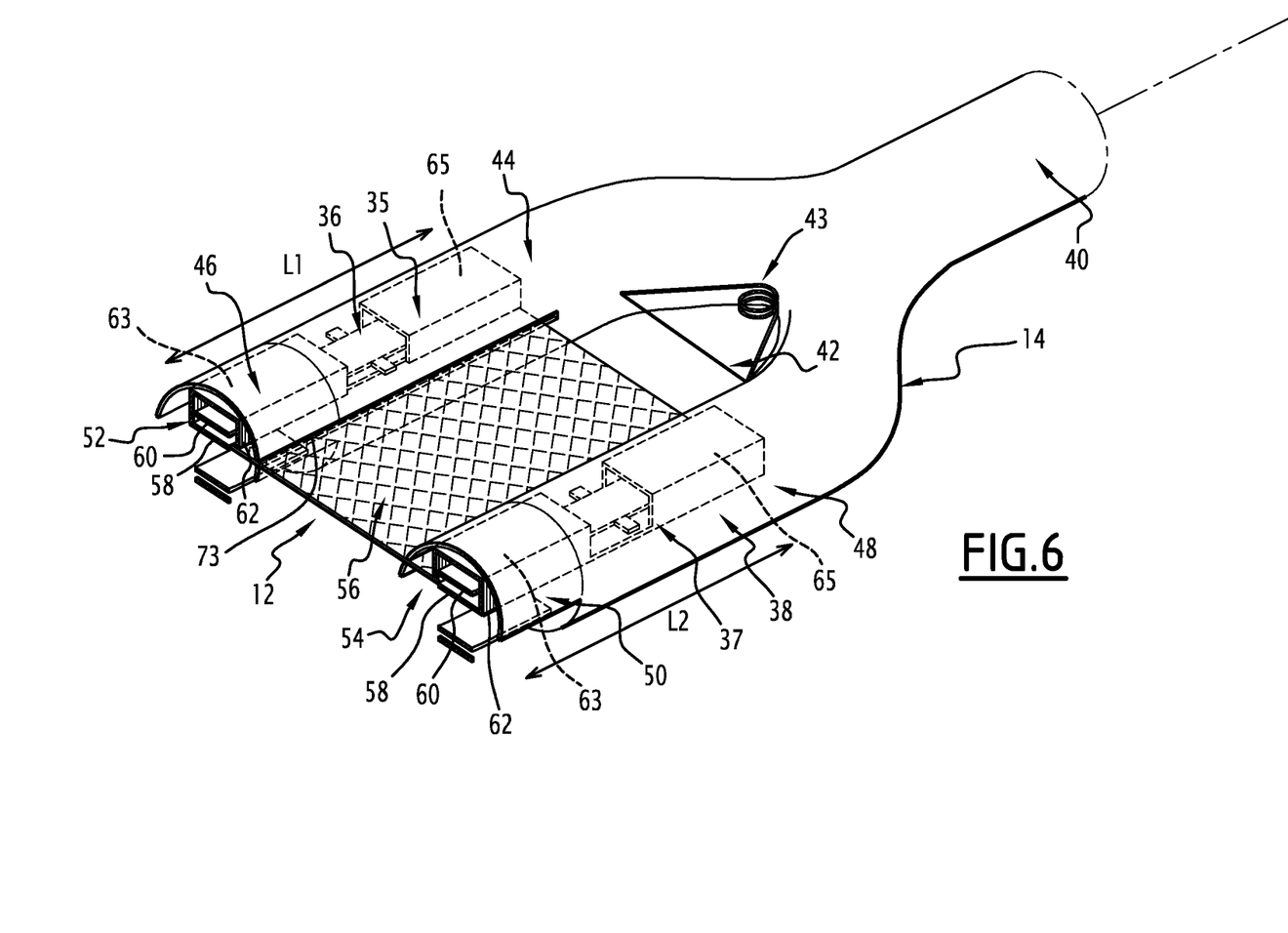
FIG. 6 is a partial sectional view of the treatment device retained in the supporting member according to a first embodiment of the invention.

As illustrated by FIG. 6, the supporting member 14 comprises a first finger 35 defining a first housing 36, a second finger 37 defining a second housing 38 and a tube 40 connecting the fingers 35, 37 together. In a deployed position, the fingers 35, 37 extend parallel with each other and in the extension of the tube 40.

Further, the supporting member 14 advantageously comprises a removable link 42 extending between both fingers 35, 37 and attached to each of its ends to each finger 35, 37. The removable link 42 is for example a flexible wire. It gives the possibility of defining a maximum separation distance between the first finger 35 and the second finger 37.

The first finger 35 has a total length L1. It comprises a cylindrical proximal portion 44 connected to the tube 40 and a distal portion 46 with the shape of an upper half-cylinder.

The cylindrical proximal portion 44 extends here over more than half of the total length L1, for example over about two thirds of the total length L1. The distal portion 46 with the shape of an upper half-cylinder extends over less than half of the total length L1, for example over about one third of the total length L1.

Similarly, the second finger 37 has a total length L2. It comprises a cylindrical proximal portion 48 connected to the tube 40 and a distal portion 50 with the shape of an upper half-cylinder.

The cylindrical proximal portion 48 extends here over more than half of the total length L2, for example over about two thirds of the total length L2. The distal portion 50 with the shape of an upper half-cylinder extends over less than half of the total length L2, for example over about one third of the total length L2.

Alternatively, the distal portions 46, 50 of the first and second fingers 35, 37 are cylindrical. The total lengths L1, L2 of each finger 35, 37 are substantially equal.

Each finger 35, 37 further includes a longitudinal side slot 73.

The supporting member 14 is advantageously made in a material such as for example nitinol. Alternatively, the supporting member 14 is made in a polymeric material.

When the supporting member 14 is entirely positioned inside the first compartment 20 of the supporting rod 16, the supporting member 14 occupies a compressed configuration in which the first and second fingers 35, 37 are side by side. Alternatively, the fingers 35, 37 overlap in the compressed configuration.

When the supporting member 14 is positioned outside the supporting rod 16, the supporting member 14 spontaneously passes towards a deployed configuration in which the first and second fingers 35, 37 substantially extend parallel with each other.

The supporting member 14 in particular comprises when it is made in a polymeric material, a spring 43 extending between both fingers 35, 37 and attached at each of its ends to each finger 35, 37. When the supporting member 14 is positioned inside the supporting rod 16, the spring 43 is in a compressed configuration. When the supporting member 14 is positioned outside the supporting rod 16, the spring is in a rest configuration. The spring 43 gives the possibility of moving apart the fingers 35, 37 when they are moved outside the supporting rod 16.

Advantageously and as visible in FIG. 6, the spring 43 is a torsion spring. Alternatively (not shown), the spring 43 is a compression spring provided with a flange able to limit the maximum separation distance between the first finger 35 and the second finger 37. The flange then plays the role of the link 42.

Figure 7:
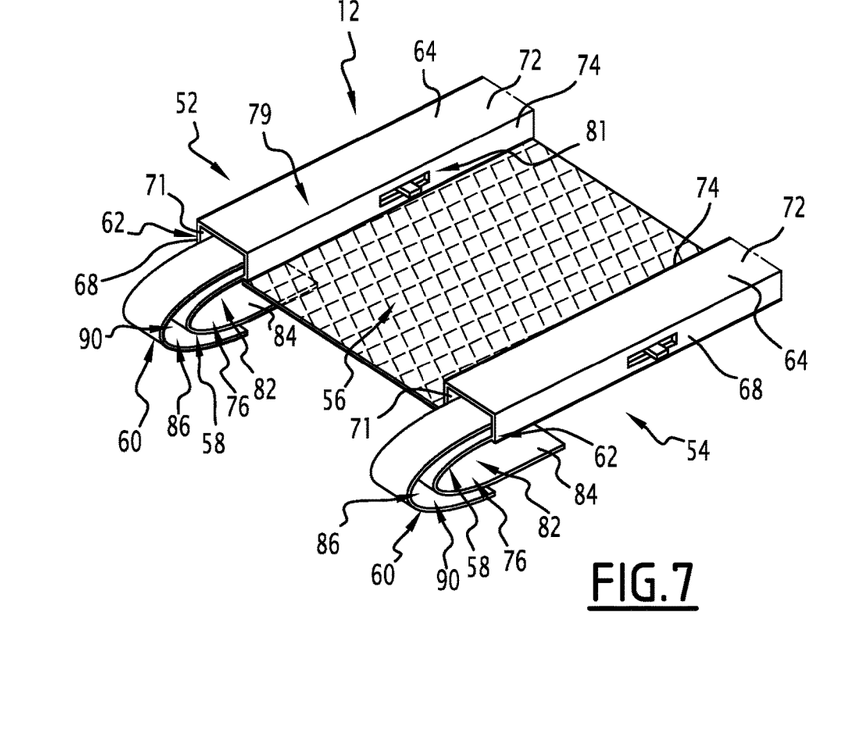
FIG. 7 is a schematic illustration of the treatment device according to an alternative of the first embodiment of the invention.
Figure 8:
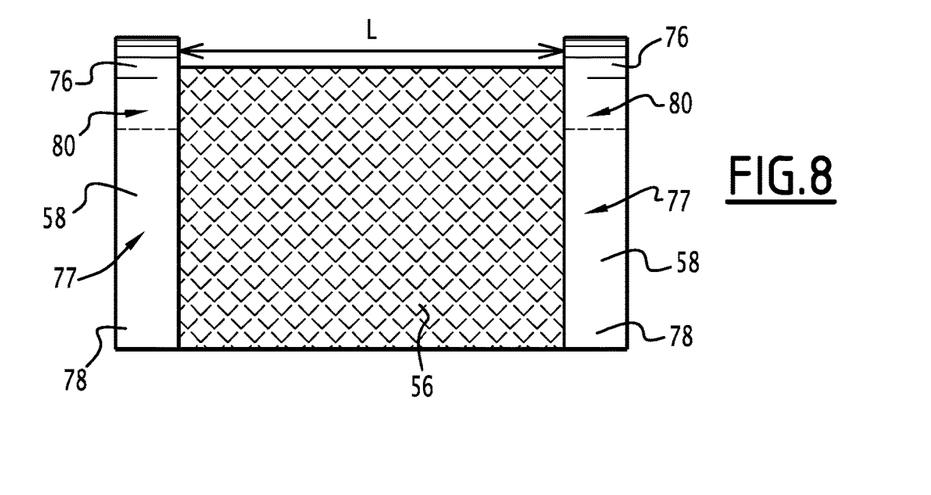
FIG. 8 is a partial schematic illustration of the treatment device according to the invention.

As illustrated by FIGS. 6 to 8, the treatment device 12 includes a first clamping assembly 52 of the leaflet 8 of the valve 4, a second clamping assembly 54 of the leaflet 8 of the valve 4 and a flexible membrane 56 connecting the clamping assemblies 52, 54 together.

The clamping assemblies 52, 54 are able to clamp a free edge 11 of the posterior leaflet 8 having the prolapse 7, each on either side of the prolapse 7. The membrane 56 extends between both clamping assemblies 52, 54.

As the first clamping assembly 52 and the second clamping assembly 54 are substantially identical, only the first clamping assembly 52 will be described subsequently.

The first clamping assembly 52 comprises a clamping arm 58, a locking member 60, and a guidance gutter 62.

With reference to FIG. 6, the gutter 62 is able to maintain assembled the locking member 60 and the clamping arm 58.

It extends along a longitudinal direction substantially parallel with the longitudinal direction of extension of the clamping arm 58 and of the locking member 60. For example it is formed with two parallelepipedal gutter portions 63, 65.

Figure 10:
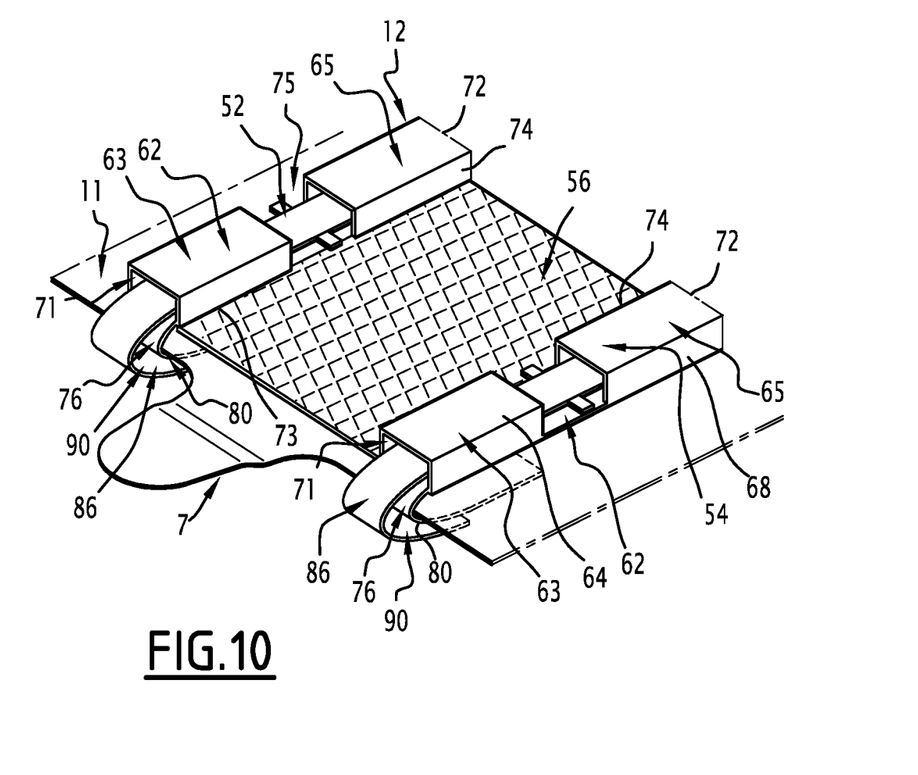
FIG. 10 is a schematic illustration of a step for operating the treatment device according to the first embodiment of the invention, the treatment device being in the rest position.

As visible in FIG. 10, each gutter portion 63, 65 comprises an upper wall 64, a lower wall formed by the clamping arm 58, and two side walls 68, 74. The walls 64, 68, 74 and the clamping arm 58 delimit a distal axial access 71 and a proximal axial access 72. The accesses 71, 72 are opposite to each other along the longitudinal direction.

Further, the gutter 62 has an intermediate aperture 75 located between both gutter portions 63, 65 and at a distance from both accesses 71, 72.

Alternatively, and as visible in FIG. 7, the gutter 62 is formed with a single parallelepipedal block 79. The parallelepipedal block 79 comprises two side apertures 81 made in the side walls 68, 74, between and at a distance from both accesses 71, 72.

With reference to FIG. 8, the clamping arm 58 comprises a distal end 76, an intermediate region 77 and a proximal end 78. The distal end 76 is hook shaped 80 curved under the membrane 56. The hook 80 defines an area 82 for inserting the free edge 11 of the posterior leaflet 8 opening facing the proximal end 78.

The distal end 76 is made in a biocompatible flexible material, for example in nitinol.

The hook 80 is thus deformable between an open configuration in which the end of the hook 80 is at a distance from the intermediate region 77 and a close configuration in which the end of the hook 80 is in contact with the intermediate region 77. In the close configuration, the hook 80 is able to clamp the free edge 11 of the posterior leaflet 8 having the prolapse 7.

Further, the hook 80 comprises an internal clamping surface 84 of the free edge 11 of the posterior leaflet 8. The clamping surface 84 advantageously comprises a plurality of protruding and recessed portions such as teeth (not shown). Alternatively, the clamping surface is smooth.

The locking member 60 comprises a distal end 86 and a proximal end 88. It further comprises a lock 92 and an abutment 94, as visible in FIG. 9. In this example, the lock 92 is located at the proximal end 88. The abutment 94 is located at a distance from the distal 86 and proximal 88 ends. It is slidably inserted into the aperture 75 of the gutter 62, as visible in FIG. 9, or in the side apertures 81, as visible in FIG. 7.

Moreover, the treatment device 12 comprises a member 96 for displacing the locking member 60 between a rest position and a locking position.

In this example, the distal end 86 is hook shaped 90 folded back around the hook 80 of the clamping arm 58. The distal end 86 of the locking member 60 extends substantially parallel with the distal end 76 of the clamping arm 58.

The distal end 86 of the locking member 60 is made in a more rigid material than the one forming the hook 80, such as for example stainless steel.

The locking member 60 extends substantially parallel to the clamping arm 58 forming the lower wall of the gutter 62. It is translationally movable relatively to the clamping arm 58 between the rest position in which the distal end 86 of the locking member 60 is at a distance from the distal end 76 of the clamping arm 58, and the locking position in which the distal end 86 of the locking member 60 exerts a force on the hook 80 of the distal end 76 of the clamping arm 58 so as to lock the hook 80 of the distal end 76 of the clamping arm 58 around the free edge 11 of the posterior leaflet 8.

Figure 9:
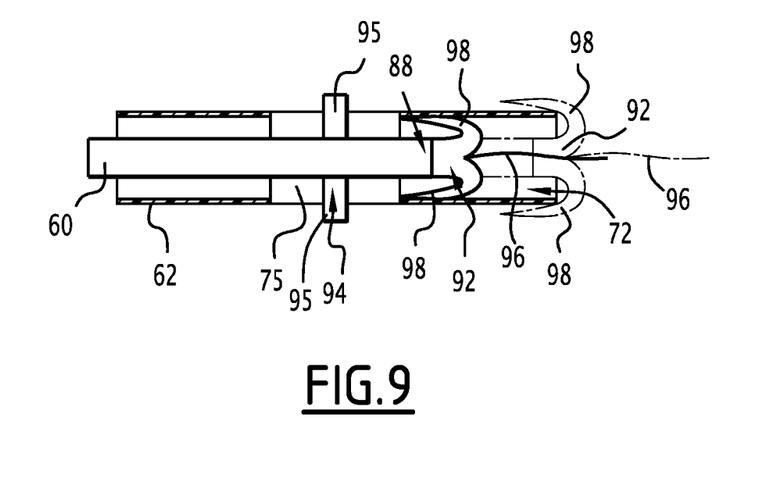
FIG. 9 is a partial longitudinal sectional view of a clamping assembly according to the first embodiment of the invention.

The abutment 94 comprises two protruding portions 95. In this example, the protruding portions extend in the extension of each other and perpendicularly to the extension direction of the locking member 60. The protruding portions are able to abut against the walls of the gutter 62 defining the aperture 75 or the side apertures 81. The abutment 94 gives the possibility of limiting the travel of the locking member 60, by preventing the locking member 60 from moving beyond the rest and locking positions.

As illustrated in FIG. 9, the lock 92 is deformable between the rest position and the locking position. It is able to lock the locking member 60 in the locking position.

More specifically, the lock 92 includes two branches 98 movable between the rest position and the locking position and extending in the extension of the proximal end 88 of the locking member 60.

When the locking member 60 is in the rest position, both branches 98 are positioned inside the gutter 62 and bent against the locking member 60. The locking member 60 is then translationally movable inside the gutter 62 and the branches 98 slide inside the gutter 62 along the side walls 68, 74.

In the locking position, the proximal end 88 is positioned outside the gutter 62 and both branches 98 are spontaneously deployed so as to extend transversely to the extension direction of the gutter 62. The branches 98 then abut against the side walls 68, 74 defining the access 72. The locking member 60 is thus blocked in the locking position.

As visible in FIG. 9, the displacement member 96 is for example a wire 96 screwed to the proximal end 88 of the locking member 60. Alternatively (not shown), the wire 96 is connected to the locking member 60 via a clamp attached to the proximal end 88 of the locking member 60. In further another alternative, the displacement member 96 is a rigid rod.

As illustrated by FIG. 8, the membrane 56 connects both clamping arms 58 to each other and is able to be held taut facing the prolapse 7 by the two clamping assemblies 52, 54.

In this example, the membrane 56 has a polygonal contour, for example rectangular contour. It extends between the clamping arms 58 and connects the side edges of the clamping arms 58, which extend parallel to each other.

When the treatment device 12 is positioned inside the supporting member 14, the membrane 56 further extends through the longitudinal side slot 73 of each finger 35, 37 of the supporting member 14.

The membrane 56 is preferably formed with a non-elastic material. Alternatively, the membrane 56 is formed with an elastic material. The membrane 56 is for example a net, a fabric, a film or a membrane. For example it is made in Gore-Tex or in pericardium.

The membrane 56 has a width L. The width L is defined here as being the dimension of the membrane 56 in the direction perpendicular to the extension direction of the clamping arms 58.

The membrane 56 has a width L comprised between 5 and 30 mm, notably comprised between 10 and 15 mm. Advantageously, the width L of the membrane 56 is less than the width of the prolapse 7. The width of the prolapse 7 is meant here as being the width on which extends the free edge of the prolapse 7. Each gutter 62 is able to be housed in the supporting member 14. The hooks 80 are received in the distal portion 46, 50 of the fingers 35, 37 and freely protrude under the supporting member 14.

Figure 12:
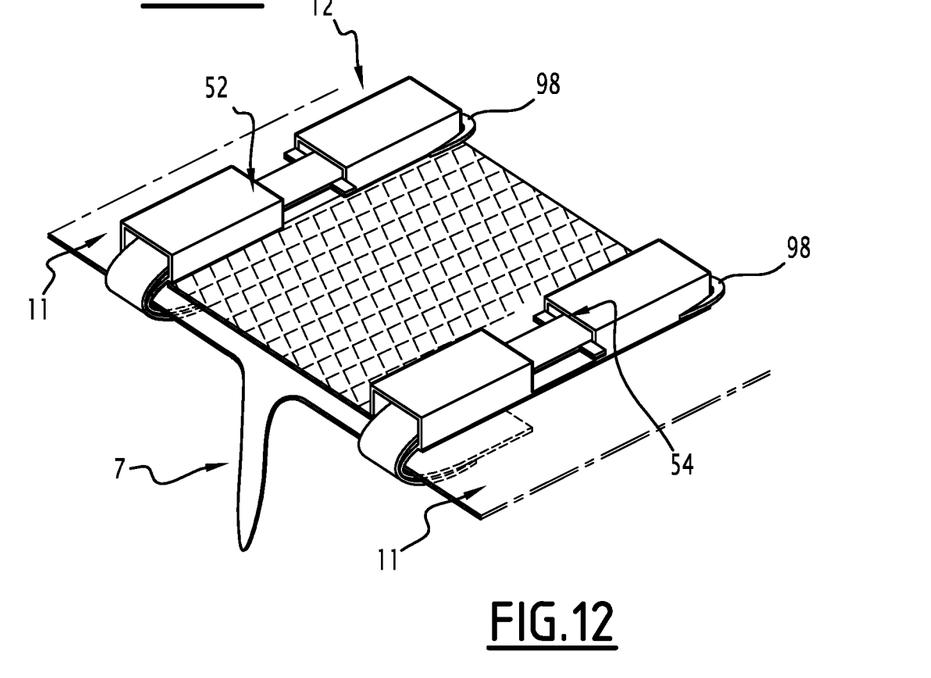
FIG. 12 is a schematic illustration of a subsequent step for operating the treatment device according to the first embodiment of the invention, the treatment device being in the locking position.

The operation of the treatment kit 2 according to the invention, during the treatment of a prolapse 7 of a mitral valve, will now be described with reference to FIGS. 12 to 14.

Initially, the treatment kit 2 is provided. The treatment device 12 is housed in the supporting member 14, which is housed in the first compartment 20 of the supporting rod 16. The supporting member 14 is maintained fixed in rotation relatively to the longitudinal axis XX' of the supporting rod 16. The tab 24 is retracted inside the second compartment 22. The supporting member 14 occupies the compressed configuration. The hooks 80 are housed in the distal portion 46, 50 of the fingers 35, 37 and freely protrude under the supporting member 14.

Next, the operator strips the supporting member 14 along the longitudinal axis XX' by withdrawing the supporting rod 16. This causes the passing of the spring 43 from its compressed configuration to its rest configuration, and the passing of the supporting member 14 from its compressed configuration to its deployed configuration. The membrane 56 is then held taut.

The withdrawal of the supporting rod 16 allows deployment of the distal ends 76 of the clamping arms 58. The latter are engaged each around a free edge 11 of the posterior leaflet 8 on either side of the prolapse 7. The free edge 11 of the leaflet 8 is inserted into the insertion area 82.

The locking members 60 are then in the rest position. More specifically, both branches 98 are positioned inside the gutter 62 and bent against the locking member 60, so that the locking member 60 is translationally movable inside the gutter 62.

Figure 11:
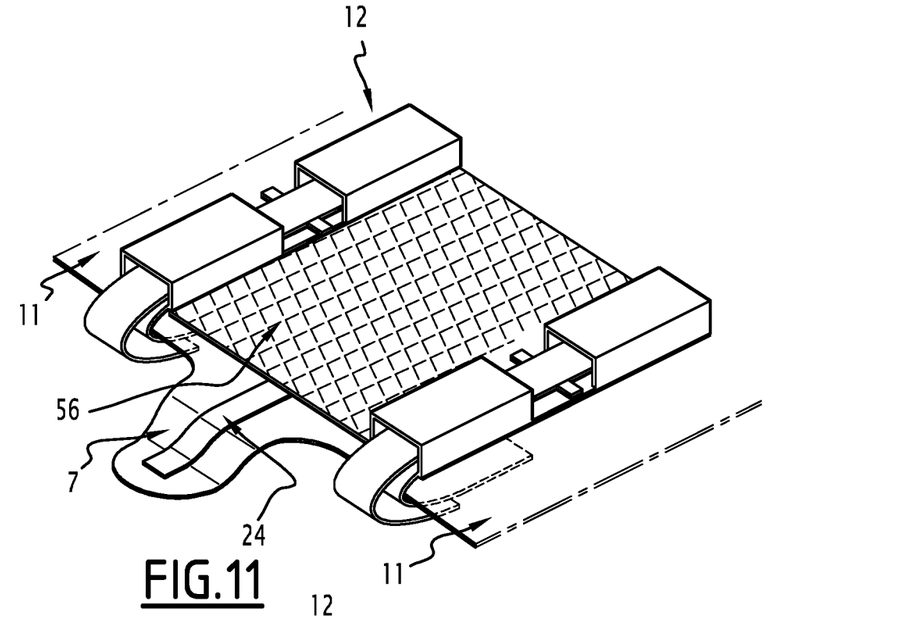
FIG. 11 is a schematic illustration of an intermediate step for operating the treatment device according to the first embodiment of the invention, the treatment device being in the rest position.

The prolapse 7 is then moved away from the membrane 56 via the tab 24, as illustrated by FIG. 11. The prolapse 7 is then maintained outside the coaptation area of the leaflets 6, 8. It protrudes away from the membrane 56.

Next, when the operator is satisfied with the positioning of the treatment device 12 on the leaflet 8, he/she definitively locks the treatment device 12 by displacing the locking members 60 to the locking position. More specifically, he/she exerts traction on the wire 96. The hooks 90 are then brought into contact with the hooks 80 and exert a force on the hooks 80 around the free edge 11 of the leaflet 8 so as to clamp the free edge 11. The proximal end 88 is displaced in the same time out of the gutter 62 through the access 72, and both branches 98 are spontaneously deployed so as to abut against the side walls 68, 74 and extend transversely to the extension direction of the gutter 62. The locking member 60 is then blocked in the locking position.

Finally, once the treatment device 12 is positioned in the body of the patient, the operator unscrews the wire 96.

Subsequently, the coaptation between the free edges of the leaflets is re-established when the valve 4 is closed. The treatment device 12 is displaceable jointly with the posterior leaflet 8 independently of the anterior leaflet 6, so that the valve 4 opens normally, without affecting the section of the aperture for letting through the blood.

It is thus conceivable that the treatment kit 2 according to the invention treats a prolapse 7 of a mitral valve in a particularly easy way and with less risk for the patient than an invasive operation.

Further, the treatment kit 2 according to the invention effectively treats the prolapse 7. Indeed, once the membrane 56 is held taut facing the prolapse 7, the mitral valve may sealably close and coaptation of the posterior and anterior leaflets is ensured, while ensuring a passage section for the blood as efficient as possible when the valve is open.

The treatment device according to the invention moreover applies more generally to the treatment of prolapse on other tissues, such as the aortic valve or the tricuspid valve.

In an alternative embodiment (not shown), each finger 35, 37 of the supporting member 14 has a shape substantially fitting the shape of the gutter 62. Each finger 35, 37 has an adjusted shape relatively to the gutter 62, so that the gutter 62 is translationally movable inside each finger 35, 37 but is maintained fixed in rotation inside the latter.

Figure 13:
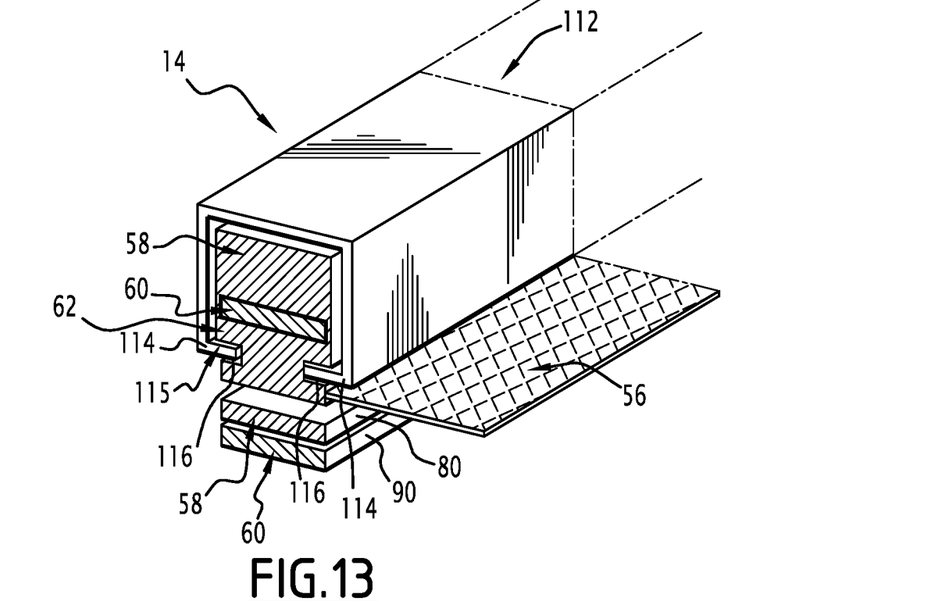
FIG. 13 is a partial sectional view of the treatment device retained in the supporting member according to a second embodiment of the invention.

A second treatment device 112 according to the invention is illustrated by FIG. 13. Unlike the first device, the supporting member 14 comprises two lower edges 114 extending over the whole of the length of each finger 35, 37 of the supporting member 14. The edges 114 define a rail 115 for sliding the gutter 62 relatively to the supporting member 14.

Further, the gutter 62 comprises two side grooves 116 extending along the gutter 62. The side grooves 116 of the gutter 62 are able to slidably receive the edges 114 of the supporting member 14. Thus, the supporting member 14 is slidably connected to the gutter 62, so that the gutter 62 is translationally movable inside each finger 35, 37 but is maintained fixed in rotation inside the latter.

The locking member 60 extends inside the gutter 62 parallel to the clamping arm 58.

Further, the protruding portions 95 (not shown) of the abutment 94 of the locking member 60 are able to abut against the side walls of the gutter 62, and have a length such that they do not extend outside the supporting member 14.

Figure 14:
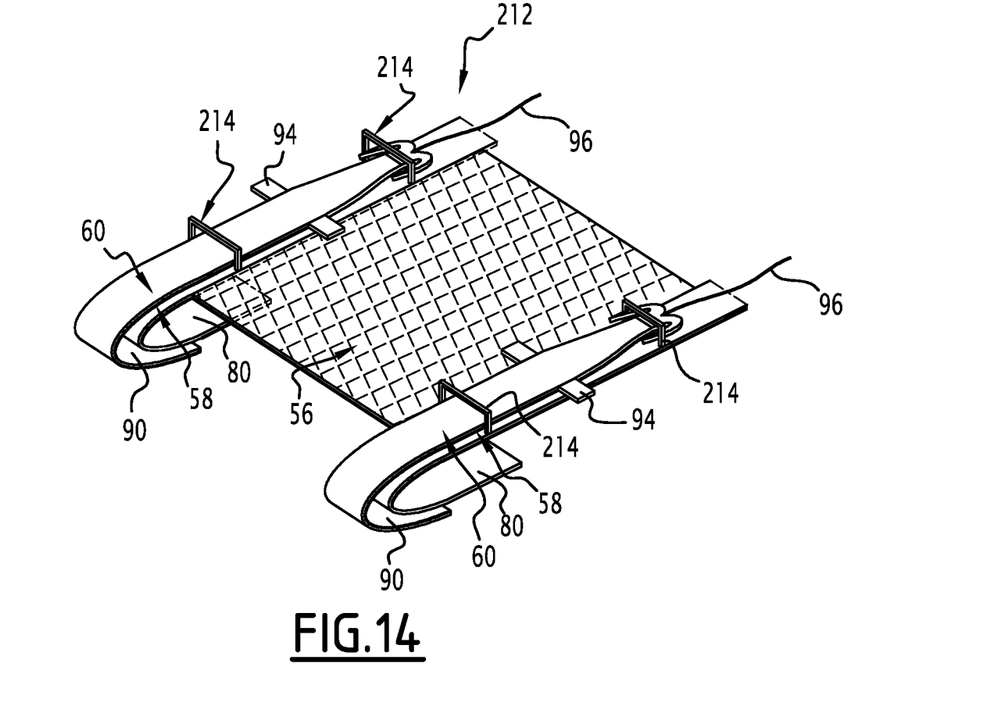
FIG. 14 is a perspective partial view of a treatment device according to a third embodiment of the invention.

A third treatment device 212 according to the invention is illustrated by FIG. 14. Unlike the first device 12, the third device 212 does not comprise any gutter.

The clamping arm 58 and the locking member 60 are maintained assembled via one or several hoops 214 fixed on the clamping arm 58.

Advantageously, the third device 212 comprises two hoops 214 attached at a distance from each other on the clamping arm 58. The locking member 60 then extends parallel to the clamping arm 58 between the clamping arm 58 and the hoops 214.

Figure 15:
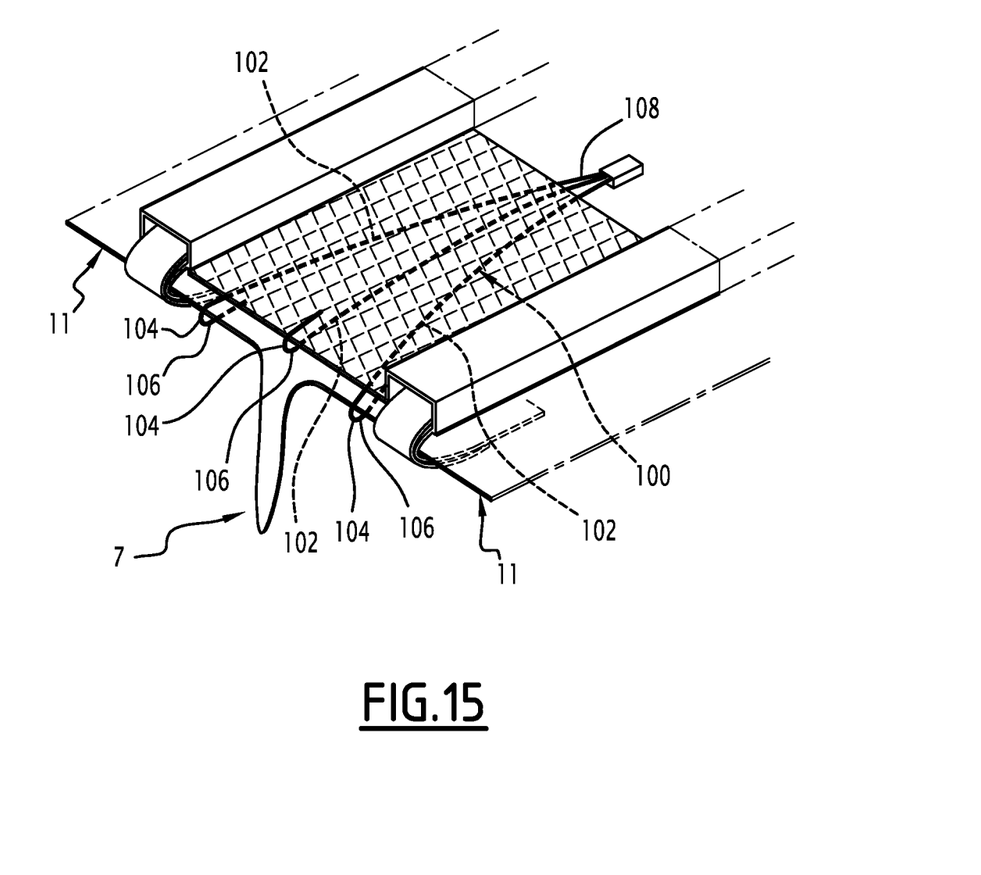
FIG. 15 is a schematic illustration of a closing device according to the invention.

In an alternative embodiment, the treatment kit 2 further includes a closing device 100 illustrated by FIG. 15. The closing device 100 comprises three arms 102 each comprising a distal end 104 shaped as a hook 106 and a common proximal end 108.

Among the three arms 102, two arms 102 are intended to hook-up with the free edge 11, each on either side of the prolapse 7, and an arm 102 is intended to hook-up with the membrane 56. The arms 102 are able to be deformed between a position in which the distal ends 104 are separated from each other, and a position in which they are brought closer to each other. In the closer position, the closing device 100 gives the possibility of reducing the space located between the prolapse 7 and the membrane 56 once the treatment device 12 is positioned on the leaflet 8, and thus allows a reduction in the risks of a leak.

The closing device 100 further comprises a locking system (not shown). The locking system is similar to the bolt 92 of the device 12. It is able to lock the closing device 100 in the close position.

In order to reduce the space located between the prolapse 7 and the membrane 56 once the device 12 has been positioned, the closing device 100 is inserted, in the separated position, between the prolapse 7 and the membrane 56.

The operator engages two hooks 106 around the free edge 11, on either side of the prolapse 7, and engages the third hook 106 around the membrane 56.

When the operator is satisfied with the positioning of the closing device 100, he/she deforms the closing device 100 in the close position, and then locks it by means of the locking system.

Alternatively, the maneuvering member 18 has a hook-shaped grasping area 26. The hook is hooked-up with a free edge of the tissue. It is driven into rotation on itself in order to hold the tissue taut before setting into place the treatment device 12.

The invention claimed is:

1. A device for treating a body tissue having a prolapse comprising:
    two clamping assemblies, each clamping assembly being able to clamp a free edge of the body tissue on either side of the prolapse and comprising:
        a clamping arm of the free edge of the body tissue, the clamping arm comprising a first flexible distal end with the shape of a hook; and
        a locking member adapted to lock the first distal end around the free edge of the body tissue, the locking member having a hook-shaped second distal end, the locking member being movable relatively to the clamping arm between a rest position in which the second distal end is at a distance from the first distal end, and a locking position in which the second distal end exerts a force on the hook of the first distal end so as to lock the hook of the first distal end around the free edge of the body tissue; and
    a membrane connecting both clamping assemblies to each other, the membrane being able to be maintained in tension facing the prolapse by the two clamping assemblies,
    wherein each clamping assembly comprises an assembling element capable of maintaining the locking member and the clamping arm in an assembled configuration,
    wherein each assembling element is formed by a gutter, the gutter being connected to the clamping arm, the locking member extending inside the gutter parallel to the clamping arm.

2. A device for treating a body tissue having a prolapse comprising:
    two clamping assemblies, each clamping assembly being able to clamp a free edge of the body tissue on either side of the prolapse and comprising:
        a clamping arm of the free edge of the body tissue, the clamping arm comprising a first flexible distal end with the shape of a hook; and
        a locking member adapted to lock the first distal end around the free edge of the body tissue, the locking member having a hook-shaped second distal end, the locking member being movable relatively to the clamping arm between a rest position in which the second distal end is at a distance from the first distal end, and a locking position in which the second distal end exerts a force on the hook of the first distal end so as to lock the hook of the first distal end around the free edge of the body tissue; and
    a membrane connecting both clamping assemblies to each other, the membrane being able to be maintained in tension facing the prolapse by the two clamping assemblies,
    wherein each clamping assembly comprises an assembling element capable of maintaining the locking member and the clamping arm in an assembled configuration, wherein each assembling element is formed with at least one hoop attached on the clamping arm, the locking member extending parallel to the clamping arm between the clamping arm and the at least one hoop.

3. A kit for treating a body tissue having a prolapse, comprising:
- a treatment device for treating a body tissue having a prolapse comprising:
  - two clamping assemblies, each clamping assembly being able to clamp a free edge of the body tissue on either side of the prolapse and comprising:
    - a clamping arm of the free edge of the body tissue, the clamping arm comprising a first flexible distal end with the shape of a hook; and
    - a locking member adapted to lock the first distal end around the free edge of the body tissue, the locking member having a hook-shaped second distal end, the locking member being movable relatively to the clamping arm between a rest position in which the second distal end is at a distance from the first distal end, and a locking position in which the second distal end exerts a force on the hook of the first distal end so as to lock the hook of the first distal end around the free edge of the body tissue; and
  - a membrane connecting both clamping assemblies to each other, the membrane being able to be maintained in tension facing the prolapse by the two clamping assemblies;
- a supporting member able to retain the treatment device; and
- a supporting rod extending along a longitudinal axis (XX') and defining at least one aperture for retaining the supporting member,
  wherein the supporting member comprises two fingers each defining a housing able to receive one of the two clamping assemblies, each finger comprising a slot intended to be crossed by the membrane.

4. The kit according to claim 3, comprising a maneuvering member movable relative to the supporting rod for maneuvering the prolapse from a position closer to the membrane to a position at a distance from the membrane.

5. The kit according to claim 4, wherein the supporting rod comprises a first compartment and a second compartment, the first and second compartments extending along the longitudinal axis, the first compartment retaining the supporting member, the second compartment retaining the maneuvering member.

6. The kit according to claim 3, wherein the body tissue is a valve leaflet.

7. The kit according to claim 6, wherein the valve leaflet is a mitral valve leaflet.

8. The kit according to claim 3 wherein, when the two fingers are outside the supporting rod, it is possible to separate the two fingers, the maximum separation distance between the two fingers being defined by a removable link or a spring.

* * * * *